United States Patent [19]

Pews et al.

[11] 4,221,913

[45] Sep. 9, 1980

[54] PREPARATION OF 2-(CHLOROMETHYL)PYRIDINE

[75] Inventors: R. Garth Pews; Mezzie L. Ash, both of Midland, Mich.

[73] Assignee: The Dow Chemical Company, Midland, Mich.

[21] Appl. No.: 15,543

[22] Filed: Feb. 26, 1979

[51] Int. Cl.$^2$ .................................... C07D 213/26
[52] U.S. Cl. ............................................. 546/346
[58] Field of Search ................................. 546/346

[56] References Cited

PUBLICATIONS

Abramovitch, Pyridine and its Derivatives, Supplement, Part Two, Wiley–Interscience, p. 457 (1974).
Matsumura, Chem. Abstracts, vol. 48, No. 11, p. 6442(b), Jun. 10, 1954.
Kato, Chem. Abstracts, vol. 50, No. 12, 8664–c to 8666–b (Jun. 25, 1956).

Primary Examiner—Alan L. Rotman
Attorney, Agent, or Firm—S. Preston Jones; Ronald G. Brookens

[57] ABSTRACT

2-(Chloromethyl)pyridine is prepared by the reaction of 2-methylpyridine-N-oxide with phosgene (carbonyl chloride) in the presence of a solvent and an acid acceptor.

7 Claims, No Drawings

PREPARATION OF 2-(CHLOROMETHYL)PYRIDINE

BACKGROUND OF THE INVENTION 2-(Chloromethyl)pyridine is a well known compound which is quite valuable as an intermediate in the preparation of various compounds which have one or more of hypocholesteremic, anti-hypotensive, anti-flammatory, analgesic, fungicidal or bactericidal properties.

DESCRIPTION OF THE PRIOR ART

A variety of processes have been employed to prepare the various mono(chloromethyl)pyridine isomers.

(Chloromethyl)pyridine compounds have been formed by the reaction of picoline-N-oxide compounds with certain chlorinating agents. The usual means of chlorinating picoline oxides is with phosphorus pentachloride or phosphoryl chloride, resulting in a mixture of 2- and 4-(chloromethyl)-pyridines. Another process is the direct chlorination of 2-picoline with chlorine but the product is contaminated with di- and trichloromethylpyridines.

T. Kato described the reaction of 2-picoline-1-oxide with phosphoryl chloride in *Yakugaku Zasshi*, 75, 1239 (1955) C.A. 50:8,665 h (1956). The reaction was run neat at temperatures of 100° C.–140° C. After separation, the residue was neutralized with potassium carbonate and extracted with ethyl ether. However, only trace amounts of 2-(chloromethyl)pyridine were obtained.

E. Matsumura, J. Chem. Soc. (Japan) 74,363 (1953), C.A. 48:6,422b (1954), described the formation of mono(chloromethyl)pyridines by the reaction of 2-picoline-1-oxide with p-toluenesulfonyl chloride.

Mathes, et al. (U.S. Pat. No. 3,123,608) describes a process for chlorinating picolines by reacting the picoline reactants with chlorine at temperatures between 40° and 80° C. in the presence of an inert solvent and an acid binding agent. The yield of 2-(chloromethyl)pyridine obtained from this was low with both di- and (trichloromethyl)pyridine compounds being also present in varying amounts.

Japanese Pat. No. 74 127,977; C.A. 84:-121,665p (1975) teaches the chlorination of 2-picoline in the presence of water, an acid acceptor and an inert solvent. This process yields 2-(chloromethyl)- and 2-(dichloromethyl)-pyridine.

SUMMARY OF THE INVENTION

The present invention is directed to the preparation of 2-(chloromethyl)pyridine by the reaction of 2-methylpyridine-N-oxide (2-picoline-N-oxide) and phosgene (carbonyl chloride) in the presence of a solvent and an acid acceptor which can be an organic or inorganic base.

In carrying out this reaction, the reactants, solvent and base are contacted and maintained together in any convenient fashion, with agitation, at a temperature of from about 3° to about 25° C. until the reaction is complete. The reaction is usually complete in from about 15 minutes to about one hour. After the reaction is complete, the reaction mixture is made basic by adding thereto an aqueous base such as sodium or potassium bicarbonate. The aqueous and organic layers are separated and the aqueous layer extracted thoroughly with solvent to remove any organic material. The organic layers are combined and the solvent removed by evaporation under reduced pressure. The product can be further purified if desired by conventional procedures of distillation, solvent washing and the like.

Inert organic hydrocarbons are normally used as the reaction solvent. Examples of such solvents include methylene chloride, methanol, ethylene dichloride, acetonitrile, tetrahydrofuran, dimethoxyethane, diethyl carbonate, p-dioxane, toluene, and the like. Methylene chloride and ethylene dichloride are preferred.

Representative acid acceptors are those compounds normally employed in this capacity and include both organic and inorganic bases such as for example, tri(loweralkyl)amines such as trimethylamine and triethylamine, pyridine, N,N-dimethylaniline, tetramethylurea and alkali alkoxides such as sodium or potassium methoxide, ethoxide, propoxide or t-butoxide.

At least an equimolar amount of phosgene is needed to react with the 2-methylpyridine-N-oxide based on the stoichiometry of the reaction. This stoichiometric ratio of reactants is normally used.

The following examples illustrate the present invention and the manner by which it can be practiced, but as such, should not be construed as limitations upon the overall scope of the same.

EXAMPLE 1

To a stirring solution of 10.9 grams (0.1 mol) of 2-picoline-N-oxide in 10 milliliters of methylene chloride at 3°–5° C. was added dropwise a solution of 9.8 grams (0.1 mol) of phosgene in 83 grams of methylene chloride. The addition took about 1 hour. To the resulting solution was added dropwise, over about 1 hour, a solution of 10.1 grams (0.1 mol) of triethylamine in 74 grams of methylene chloride. Analysis of the product by gas chromatography (g.c.) showed a yield of 3.48 grams of the desired 2-(chloromethyl)pyridine (71% conversion of the 2-picoline-N-oxide with 27% selectivity to the above isomer).

EXAMPLE 2

To a stirring solution of 10.9 grams (0.1 mol) of 2-picoline-N-oxide in 10 milliliters of methylene chloride was added dropwise a solution of 9.8 grams (0.1 mol) of phosgene in 83 grams of methylene chloride at 25° C. At the completion of the addition, the resulting solution was stirred for about 30 minutes and then a solution of 10.1 grams (0.1 mol) of triethylamine in 74 grams of methylene chloride was added thereto dropwise. Analysis of the product by gas chromatography (g.c.) showed a 55% conversion of the 2-picoline-N-oxide with 24% selectivity to the desired 2-(chloromethyl)pyridine isomer.

EXAMPLE 3

To a stirring solution of 10.9 grams (0.1 mol) of 2-picoline-N-oxide in 10 milliliters of methylene chloride was added dropwise a solution of 9.8 grams (0.1 mol) of phosgene in 83 grams of methylene chloride at 25° C. At the completion of the addition the solution was cooled to 5° C. To the resulting solution was added dropwise a solution of 10.1 grams (0.1 mol) of triethylamine in 74 grams of methylene chloride. Analysis of the product by gas chromatography (g.c.) showed 55% conversion of the 2-picoline-N-oxide with 28% selectivity to the desired 2-(chloromethyl)pyridine isomer.

EXAMPLE 4

To a stirring solution of 10.9 grams (0.1 mol) of 2-picoline-N-oxide in 10 milliliters of methylene chloride was added dropwise a solution of 9.8 grams (0.1 mol) phosgene in 74 grams of methylene chloride at 25° C. The resulting solution was stirred for 10 minutes. The resulting solution was divided into 10 milliliter aliquots and to each aliquot was added 0.01 mols of one of the hereinafter set forth acid acceptors. The solutions were analyzed by g.c. to determine the percent conversion and the percent selective conversion to the desired 2-(chloromethyl)pyridine. The results of this analysis is set forth below in Table 1.

TABLE 1
CONVERSION OF 2-PICOLINE-N-OXIDE WITH PHOSGENE TO 2-(CHLOROMETHYL)PYRIDINE

| Acid Acceptor | Percent Conversion of 2-picoline-N-oxide | Percent Selectivity of Conversion to 2-(chloromethyl) pyridine |
|---|---|---|
| Pyridine | 74.9 | 37.8 |
| Triethylamine | 67.4 | 45.4 |
| Sodium methoxide | 33.5 | 59.4 |
| Potassium t-butoxide | 27.8 | 74.0 |
| Caustic (Na) powder | 38.8 | 55.2 |
| N,N-dimethylaniline | 69.9 | 39.6 |
| Isopropanolamine | 34.6 | 51.0 |
| Tetramethylurea | 64.8 | 45.1 |
| Sodium acetate | 43.2 | 48.6 |
| 1,8-bis-(dimethylamino)-naphthalene | 80.0 | 32.0 |

EXAMPLE 5

To a stirring solution of 10.9 grams (0.1 mol) of 2-picoline-N-oxide in 10 milliliters of methylene chloride was added dropwise at 25° C., a solution of 9.8 grams (0.1 mol) of phosgene in 83 grams of methylene chloride. The resulting solution was divided into 10 milliliter aliquots and to each aliquot was added 35 milliliters of one of the hereinafter set forth solvents. The solutions were mixed well and 1.0 gram (0.01 mol) of triethylamine was added to each mixture. The solutions were analyzed by g.c. to determine the percent conversion and the percent selective conversion to the desired 2-(chloromethyl)pyridine. The results of this analysis is set forth below in Table 2.

TABLE 2
CONVERSION OF 2-PICOLINE-N-OXIDE WITH PHOSGENE TO 2-(CHLOROMETHYL)PYRIDINE

| Solvent | Percent Conversion of 2-picoline-N-oxide | Percent Selectivity of Conversion to 2-(chloromethyl)pyridine |
|---|---|---|
| Methylene chloride | 68.8 | 32.4 |
| Methanol | 60.0 | 26.5 |
| Acetonitrile | 57.8 | 61.0 |
| Toluene | 100.0 | 12.0 |
| P-Dioxane | 64.3 | 35.3 |
| Nitrobenzene | 57.7 | 37.8 |
| Tetrahydrofuran | 77.4 | 26.7 |
| Dimethoxyethane | 66.4 | 27.7 |

What is claimed is:

1. A process for preparing 2-(chloromethyl)pyridine which comprises reacting by contacting 2-methylpyridine-N-oxide with phosgene in the presence of a solvent selected from the group consisting of methylene chloride, methanol, acetonitrile, toluene, p-dioxane, nitrobenzene, tetrahydrofuran, dimethoxy ethane, ethylene dichloride and diethyl carbonate and an acid acceptor at a temperature of from about 3° to about 25° C.

2. A process as defined in claim 1 wherein the solvent is methylene chloride.

3. A process as defined in claim 1 wherein the solvent is acetonitrile.

4. A process as defined in claim 1 wherein the acid acceptor is triethylamine.

5. A process as defined in claim 1 wherein the acid acceptor is pyridine.

6. The process as defined in claim 4 wherein the solvent is methylene chloride.

7. The process as defined in claim 4 wherein the solvent is acetonitrile.

* * * * *